(12) United States Patent
Yonemura et al.

(10) Patent No.: US 11,252,962 B2
(45) Date of Patent: *Feb. 22, 2022

(54) CYCLOPROPYLPYRIDYL GROUP-CONTAINING BENZIMIDAZOLE COMPOUND OR SALT THEREOF, AGRICULTURAL AND HORTICULTURAL INSECTICIDE COMPRISING THE COMPOUND OR THE SALT, AND METHOD FOR USING THE INSECTICIDE

(71) Applicant: NIHON NOHYAKU CO., LTD., Tokyo (JP)

(72) Inventors: Ikki Yonemura, Osaka (JP); Shunpei Fujie, Osaka (JP); Ryosuke Tanaka, Osaka (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 70 days.

This patent is subject to a terminal disclaimer.

(21) Appl. No.: 16/648,714

(22) PCT Filed: Sep. 20, 2018

(86) PCT No.: PCT/JP2018/034703
§ 371 (c)(1),
(2) Date: Mar. 19, 2020

(87) PCT Pub. No.: WO2019/059244
PCT Pub. Date: Mar. 28, 2019

(65) Prior Publication Data
US 2020/0214292 A1 Jul. 9, 2020

(30) Foreign Application Priority Data

Sep. 21, 2017 (JP) .............................. JP2017-181010
Apr. 3, 2018 (JP) .............................. JP2018-071776
Apr. 25, 2018 (JP) .............................. JP2018-084519

(51) Int. Cl.
*A01N 43/52* (2006.01)
*C07D 401/04* (2006.01)

(52) U.S. Cl.
CPC ........... *A01N 43/52* (2013.01); *C07D 401/04* (2013.01)

(58) Field of Classification Search
CPC ............................ C07D 401/04; A01N 43/52
See application file for complete search history.

(56) References Cited

U.S. PATENT DOCUMENTS

| | | |
|---|---|---|
| 2015/0366208 A1 | 12/2015 | Shimizu et al. |
| 2016/0021886 A1 | 1/2016 | Yonemura et al. |
| 2017/0233389 A1 | 8/2017 | Jung et al. |
| 2017/0260214 A1 | 9/2017 | Stoller et al. |
| 2017/0318809 A1 | 11/2017 | Edmunds et al. |
| 2017/0342065 A1 | 11/2017 | Hueter et al. |
| 2018/0002347 A1* | 1/2018 | Yonemura .............. A01N 43/78 |
| 2018/0334456 A1 | 11/2018 | Jung et al. |
| 2019/0045786 A1 | 2/2019 | Matsuo et al. |
| 2019/0308971 A1 | 10/2019 | Hueter et al. |

FOREIGN PATENT DOCUMENTS

| | | | |
|---|---|---|---|
| JP | WO 2016-121997 | * | 8/2016 |
| JP | 2017-526667 | | 9/2017 |
| WO | 2014/119679 | | 8/2014 |
| WO | 2014/142292 | | 9/2014 |
| WO | 2016/026848 | | 2/2016 |
| WO | 2016/071214 | | 5/2016 |
| WO | 2016/096584 | | 6/2016 |
| WO | 2016/104746 | | 6/2016 |

(Continued)

OTHER PUBLICATIONS

International Preliminary Report on Patentability dated Mar. 24, 2020 in International (PCT) Patent Application No. PCT/JP2018/034703.

(Continued)

*Primary Examiner* — Valerie Rodriguez-Garcia
(74) *Attorney, Agent, or Firm* — Wenderoth, Lind & Ponack, L.L.P.

(57) ABSTRACT

In crop production in the fields of agriculture, horticulture and the like, the damage caused by insect pests etc. is still immense, and insect pests resistant to existing insecticides have emerged. The present invention has been made in view of such circumstances, and an object of the present invention is to develop and provide a novel agricultural and horticultural insecticide. The present invention provides a benzimidazole compound represented by the general formula (1):

[Chem. 1]

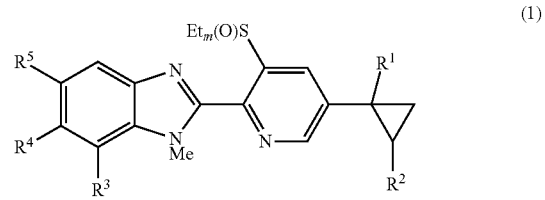

(1)

{wherein $R^1$ represents a hydrogen atom or a cyano group, $R^2$ and $R^3$ each represent a hydrogen atom, $R^4$ represents a hydrogen atom or a haloalkoxy group, $R^5$ represents a haloalkoxy group, a haloalkylthio group, a haloalkylsulfinyl group, or a haloalkylsulfonyl group, and m represents 0 or 2}, or a salt thereof; an agricultural and horticultural insecticide comprising the compound or the salt as an active ingredient; and a method for using the insecticide.

12 Claims, No Drawings

(56) References Cited

FOREIGN PATENT DOCUMENTS

WO      2016/121997      8/2016
WO      2017/146226      8/2017

OTHER PUBLICATIONS

International Search Report dated Nov. 27, 2018 in corresponding International (PCT) Application No. PCT/JP2018/034703.

* cited by examiner

CYCLOPROPYLPYRIDYL GROUP-CONTAINING BENZIMIDAZOLE COMPOUND OR SALT THEREOF, AGRICULTURAL AND HORTICULTURAL INSECTICIDE COMPRISING THE COMPOUND OR THE SALT, AND METHOD FOR USING THE INSECTICIDE

TECHNICAL FIELD

The present invention relates to a cyclopropylpyridyl group-containing benzimidazole compound or a salt thereof, an agricultural and horticultural insecticide comprising the compound or the salt as an active ingredient, and a method for using the insecticide.

BACKGROUND ART

Various compounds have been examined for their potential as agricultural and horticultural insecticides, and among them, certain kinds of cyclopropylpyridyl compounds have been reported to be useful as insecticides (for example, see Patent Literature 1 to 5). The literature, however, does not disclose any compound in which a cyclopropylpyridyl group is bound to a benzimidazole ring.

CITATION LIST

Patent Literature

Patent Literature 1: WO 2016/026848
Patent Literature 2: WO 2016/071214
Patent Literature 3: WO 2016/096584
Patent Literature 4: WO 2016/104746
Patent Literature 5: WO 2016/121997

SUMMARY OF INVENTION

Technical Problem

In crop production in the fields of agriculture, horticulture and the like, the damage caused by insect pests etc. is still immense. Addressing this issue requires agricultural and horticultural insecticides which are useful in terms of control of emerged drug-resistant insect pests, limitation of impact on bioindicators, labor-saving of operation, securing of operator's safety, etc.; and which are also characterized by having less impact on natural predatory and useful insects; being active as systemic insecticides; having low toxicity for mammals including humans; having less impact on bioindicators such as fish and useful insects; having a similar effect across different species; and the like. Therefore, the development of novel agricultural and horticultural insecticides having such excellent properties is desired.

Solution to Problem

The present inventors conducted extensive research to solve the above-mentioned problems. As a result, the present inventors found that the cyclopropylpyridyl group-containing benzimidazole compound represented by the general formula (1) or a salt thereof is very useful as a solution to the above-mentioned problems in that the compound or the salt is not only highly effective for the control of agricultural and horticultural pests, but also has little impact on nontarget organisms such as natural predators and useful insects.

Based on this finding, the present inventors completed the present invention.

That is, the present invention includes the following.

[1] A benzimidazole compound represented by the general formula (1)

[Chem. 1]

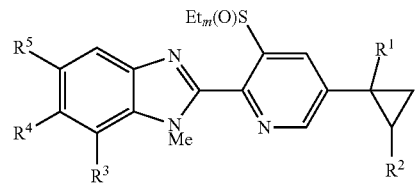

(1)

{wherein
R$^1$ and R$^2$ may be the same or different, and each represent
(a1) a hydrogen atom;
(a2) a cyano group; or
(a3) a C(R$^6$)=NOR$^7$ group (wherein R$^6$ represents (e1) a hydrogen atom, and R$^7$ represents (f1) a halo ($C_1$-$C_6$) alkyl group),
R$^3$ represents
(b1) a hydrogen atom;
(b2) a halogen atom;
(b3) a ($C_1$-$C_6$) alkyl group; or
(b4) a ($C_1$-$C_6$) alkoxy group,
R$^4$ represents
(c1) a hydrogen atom;
(c2) a halogen atom;
(c3) a halo ($C_1$-$C_6$) alkylthio group;
(c4) a halo ($C_1$-$C_6$) alkylsulfinyl group;
(c5) a halo ($C_1$-$C_6$) alkylsulfonyl group; or
(c6) a halo ($C_1$-$C_6$) alkoxy group,
R$^5$ represents
(d1) a hydrogen atom;
(d2) a halo ($C_1$-$C_6$) alkyl group;
(d3) a halo ($C_1$-$C_6$) alkoxy group;
(d4) a halo ($C_1$-$C_6$) alkylthio group;
(d5) a halo ($C_1$-$C_6$) alkylsulfinyl group; or
(d6) a halo ($C_1$-$C_6$) alkylsulfonyl group, and
m represents 0, 1, or 2}, or
a salt thereof.
[2] The benzimidazole compound represented by the general formula (1) shown above,
{wherein
R$^1$ and R$^2$ may be the same or different, and each represent
(a1) a hydrogen atom;
(a2) a cyano group; or
(a3) a C(R$^6$)=NOR$^7$ group (wherein R$^6$ represents (e1) a hydrogen atom, and R$^7$ represents (f1) a halo ($C_1$-$C_6$) alkyl group),
R$^3$ represents
(b1) a hydrogen atom;
(b2) a halogen atom;
(b3) a ($C_1$-$C_6$) alkyl group; or
(b4) a ($C_1$-$C_6$) alkoxy group,
R$^4$ represents
(c1) a hydrogen atom;
(c2) a halogen atom;
(c3) a halo ($C_1$-$C_6$) alkylthio group;
(c4) a halo ($C_1$-$C_6$) alkylsulfinyl group; or
(c5) a halo ($C_1$-$C_6$) alkylsulfonyl group, $R^5$ represents
(d1) a hydrogen atom;
(d2) a halo ($C_1$-$C_6$) alkyl group;
(d3) a halo ($C_1$-$C_5$) alkoxy group;
(d4) a halo ($C_1$-$C_5$) alkylthio group;
(d5) a halo ($C_1$-$C_6$) alkylsulfinyl group; or
(d6) a halo ($C_1$-$C_6$) alkylsulfonyl group, and
m represents 0, 1, or 2}.

[3] The benzimidazole compound or the salt according to the above [13], wherein
$R^1$ and $R^2$ may be the same or different, and each represent
(a1) a hydrogen atom;
(a2) a cyano group; or
(a3) a $C(R^6)$=$NOR^7$ group (wherein $R^6$ represents (e1) a hydrogen atom, and $R^7$ represents (f1) a halo ($C_1$-$C_6$) alkyl group),
$R^3$ represents
(b1) a hydrogen atom;
(b2) a halogen atom;
(b3) a ($C_1$-$C_6$) alkyl group; or
(b4) a ($C_1$-$C_6$) alkoxy group,
$R^2$ represents
(c1) a hydrogen atom;
(c2) a halogen atom;
(c3) a halo ($C_1$-$C_6$) alkylthio group; or
(c6) a halo ($C_1$-$C_6$) alkoxy group, and
$R^5$ represents
(d1) a hydrogen atom;
(d2) a halo ($C_1$-$C_6$) alkyl group;
(d3) a halo ($C_1$-$C_6$) alkoxy group;
(d4) a halo ($C_1$-$C_6$) alkylthio group;
(d5) a halo ($C_1$-$C_6$) alkylsulfinyl group; or
(d6) a halo ($C_1$-$C_6$) alkylsulfonyl group.

[4] The benzimidazole compound or the salt according to the above [1], wherein
$R^1$ and $R^2$ may be the same or different, and each represent
(a1) a hydrogen atom; or
(a2) a cyano group,
$R^3$ represents (b1) a hydrogen atom,
$R^4$ represents
(c1) a hydrogen atom;
(c2) a halogen atom;
(c3) a halo ($C_1$-$C_6$) alkylthio group; or
(c6) a halo ($C_1$-$C_6$) alkoxy group, and
$R^5$ represents
(d1) a hydrogen atom;
(d2) a halo ($C_1$-$C_6$) alkyl group;
(d3) a halo ($C_1$-$C_6$) alkoxy group;
(d4) a halo ($C_1$-$C_6$) alkylthio group;
(d5) a halo ($C_1$-$C_6$) alkylsulfinyl group; or
(d6) a halo ($C_1$-$C_6$) alkylsulfonyl group.

[5] The benzimidazole compound or the salt according to the above [1], wherein
$R^1$ and $R^2$ each represent (a1) a hydrogen atom,
$R^3$ represents (b1) a hydrogen atom,
$R^4$ represents
(c1) a hydrogen atom;
(c3) a halo ($C_1$-$C_6$) alkylthio group; or
(c6) a halo ($C_1$-$C_6$) alkoxy group, and
$R^5$ represents
(d2) a halo ($C_1$-$C_6$) alkyl group;
(d3) a halo ($C_1$-$C_6$) alkoxy group;
(d4) a halo ($C_1$-$C_6$) alkylthio group;
(d5) a halo ($C_1$-$C_5$) alkylsulfinyl group; or
(d6) a halo ($C_1$-$C_6$) alkylsulfonyl group.

[6] The benzimidazole compound or the salt according to the above [1], wherein
$R^1$ represents (a2) a cyano group,
$R^2$ represents (a1) a hydrogen atom,
$R^3$ represents (b1) a hydrogen atom,
$R^4$ represents (c1) a hydrogen atom, and
$R^5$ represents
(d4) a halo ($C_1$-$C_6$) alkylthio group;
(d5) a halo ($C_1$-$C_6$) alkylsulfinyl group; or
(d6) a halo ($C_1$-$C_6$) alkylsulfonyl group.

[7] The benzimidazole compound or the salt according to the above [1], wherein
$R^1$ represents (a2) a cyano group,
$R^2$ represents (a1) a hydrogen atom,
$R^3$ represents (b1) a hydrogen atom,
$R^4$ represents
(c1) a hydrogen atom; or
(c3) a halo ($C_1$-$C_6$) alkylthio group, and
$R^5$ represents
(d2) a halo ($C_1$-$C_6$) alkyl group;
(d3) a halo ($C_1$-$C_6$) alkoxy group;
(d4) a halo ($C_1$-$C_6$) alkylthio group;
(d5) a halo ($C_1$-$C_6$) alkylsulfinyl group; or
(d6) a halo ($C_1$-$C_5$) alkylsulfonyl group.

[8] An agricultural and horticultural insecticide comprising the benzimidazole compound or the salt according to any of the above [1] to [7] as an active ingredient.

[9] A method for using an agricultural and horticultural insecticide, the method comprising treating plants or soil with an effective amount of the benzimidazole compound or the salt according to any of the above [1] to [7].

[10] An animal ectoparasite control agent comprising the benzimidazole compound or the salt according to any of the above [1] to [7] as an active ingredient.

[11] An animal endoparasite control agent comprising the benzimidazole compound or the salt according to any of the above [1] to [7] as an active ingredient.

Advantageous Effects of Invention

The cyclopropylpyridyl group-containing benzimidazole compound of the present invention or a salt thereof is not only highly effective as an agricultural and horticultural insecticide but also effective for the disinfection of pests which live in the interior of or on the exterior of pets such as dogs and cats and domestic animals such as cattle and sheep.

DESCRIPTION OF EMBODIMENTS

In the definition of the benzimidazole compound represented by the general formula (1) of the present invention or a salt thereof, "halo" refers to a "halogen atom" and represents a fluorine atom, a chlorine atom, a bromine atom or an iodine atom.

The "($C_1$-$C_6$) alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, an 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like.

The "($C_1$-$C_6$) alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, an 1-ethylpropyloxy group, a 1-methylbutyloxy group, a n-hexyloxy group, an isohexyloxy group, a 1,1,2-trimethylpropyloxy group or the like.

The "($C_1$-$C_6$) alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, an 1-ethylpropylthio group, a 1-methylbutylthio group, a n-hexylthio group, an isohexylthio group, a 1,1,2-trimethylpropylthio group or the like. The "($C_1$-$C_5$) alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, an 1-ethylpropylsulfinyl group, a 1-methylbutylsulfinyl group, a n-hexylsulfinyl group, an isohexylsulfinyl group, a 1,1,2-trimethylpropylsulfinyl group or the like. The "($C_1$-$C_6$) alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, an 1-ethylpropylsulfonyl group, a 1-methylbutylsulfonyl group, a n-hexylsulfonyl group, an isohexylsulfonyl group, a 1,1,2-trimethylpropylsulfonyl group or the like.

The above-mentioned "($C_1$-$C_6$) alkyl group", "($C_1$-$C_6$) alkoxy group", "($C_1$-$C_6$) alkylthio group", "($C_1$-$C_6$) alkylsulfinyl group", and "($C_1$-$C_6$) alkylsulfonyl group" may be substituted with one or more halogen atoms at a substitutable position(s) in place of a hydrogen atom(s), and in the case where any of the above-listed groups is substituted with two or more halogen atoms, the halogen atoms may be the same or different.

The above-mentioned "groups substituted with one or more halogen atoms" are expressed as a "halo ($C_1$-$C_6$) alkyl group", a "halo ($C_1$-$C_6$) alkoxy group", a "halo ($C_1$-$C_6$) alkylthio group", a "halo ($C_1$-$C_6$) alkylsulfinyl group", and a "halo ($C_1$-$C_6$) alkylsulfonyl group". The above definitions and examples of each group in the present invention are all obvious to those skilled in the art.

The expression "($C_1$-$C_6$)" refers to the range of the number of carbon atoms in each group.

Examples of the salt of the benzimidazole compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The benzimidazole compound represented by the general formula (1) of the present invention and a salt thereof can have one or more chiral centers in the structural formula, and can exist as two or more kinds of optical isomers or diastereomers. All the optical isomers and mixtures of the isomers at any ratio are also included in the present invention. Further, the benzimidazole compound represented by the general formula (1) of the present invention and a salt thereof can exist as two kinds of geometric isomers due to a carbon-nitrogen double bond in the structural formula. All the geometric isomers and mixtures of the isomers at any ratio are also included in the present invention.

In a preferable embodiment of the benzimidazole compound represented by the general formula (1) of the present invention or a salt thereof, $R^1$ and $R^2$ may be the same or different, and are each (a1) a hydrogen atom;

(a2) a cyano group; or (a3) a $C(R^E)$=$NOR^7$ group (wherein $R^6$ is (e1) a hydrogen atom, and $R^7$ is (f1) a halo ($C_1$-$C_6$) alkyl group), $R^3$ is (b1) a hydrogen atom;

(b2) a halogen atom;

(b3) a ($C_1$-$C_6$) alkyl group; or (b4) a ($C_1$-$C_6$) alkoxy group, $R^4$ is (c1) a hydrogen atom;

(c2) a halogen atom;

(c3) a halo ($C_1$-$C_6$) alkylthio group; or (c6) a halo ($C_1$-$C_6$) alkoxy group, and $R^5$ is (d1) a hydrogen atom;

(d2) a halo ($C_1$-$C_6$) alkyl group;

(d3) a halo ($C_1$-$C_6$) alkoxy group;

(d4) a halo ($C_1$-$C_6$) alkylthio group;

(d5) a halo ($C_1$-$C_6$) alkylsulfinyl group; or (d6) a halo ($C_1$-$C_6$) alkylsulfonyl group.

More preferably, $R^1$ is (a1) a hydrogen atom; or (a2) a cyano group, $R^2$ is (a1) a hydrogen atom, $R^3$ is (b1) a hydrogen atom, $R^4$ is (c1) a hydrogen atom; or (c6) a halo ($C_1$-$C_6$) alkoxy group, and $R^5$ is (d2) a halo ($C_1$-$C_6$) alkyl group;

(d3) a halo ($C_1$-$C_6$) alkoxy group;

(d4) a halo ($C_1$-$C_6$) alkylthio group;

(d5) a halo ($C_1$-$C_6$) alkylsulfinyl group; or (d6) a halo ($C_1$-$C_6$) alkylsulfonyl group.

The benzimidazole compound of the present invention or a salt thereof (hereinafter may be abbreviated simply as a benzimidazole compound) can be produced according to, for example, the production methods described below, which are non-limiting examples. The starting compounds used in the production methods of the present invention can be produced by known methods or methods known per se.

Production Method 1

[Chem. 2]

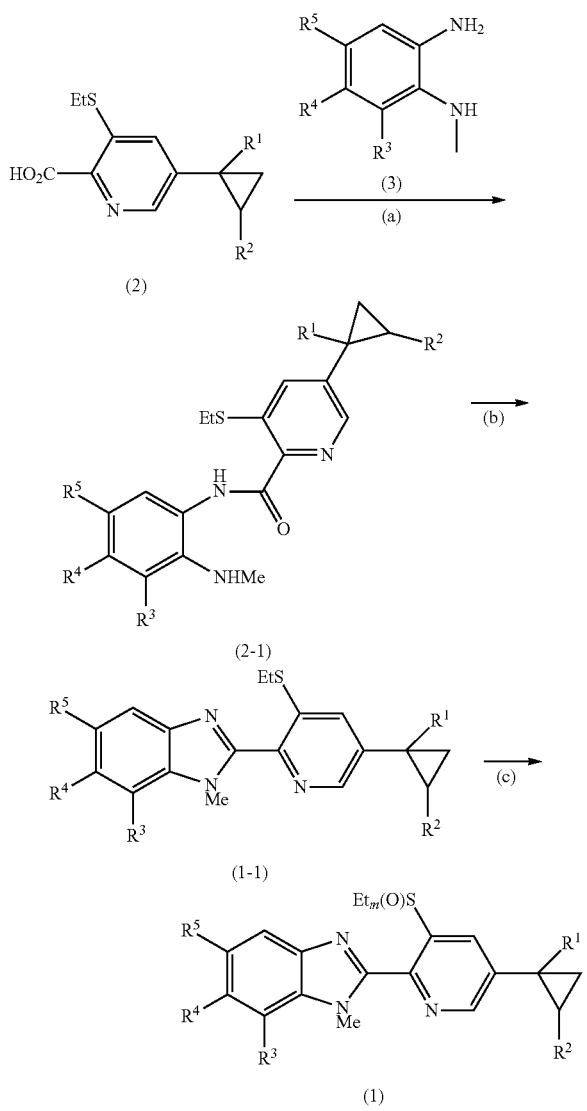

In the formula, $R^1$, $R^2$, $R^3$, $R^4$, $R^5$, and m are as defined above.

Production Method at Step [a]

The amide compound represented by the general formula (2-1) can be produced by reacting the carboxylic acid represented by the general formula (2) with the diamino compound represented by the general formula (3) in the presence of a condensing agent, a base, and an inert solvent. The desired compound (2-1), which may or may not be isolated, is subjected to the reaction in the following step (b).

Examples of the condensing agent used in this reaction include diethyl phosphorocyanidate (DEPC), carbonyldiimidazole (CDI), 1,3-dicyclohexylcarbodiimide (DCC), chlorocarbonic esters and 2-chloro-1-methylpyridinium iodide. The amount of the condensing agent used is appropriately selected from the range of a 1- to 1.5-fold molar amount relative to the compound represented by the general formula (2).

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (2).

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture.

Since this reaction is an equimolar reaction of the reactants, they are basically used in equimolar amounts, but either of them may be used in an excess amount. The reaction temperature may be in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by the usual method. As needed, recrystallization, column chromatography, etc. can be employed for the purification of the compound of interest. Alternatively, the post-reaction mixture may be directly subjected to the next step without intermediate isolation.

Production Method at Step [b]

The benzimidazole compound represented by the general formula (1-1) can be produced by reacting the amide compound of the general formula (2-1) produced by the production method at step [a] in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; and phosphoric acid. The amount of the acid used is appropriately selected from the range of a 0.01- to 10-fold molar amount relative to the amide compound represented by the general formula (2-1).

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture.

After the reaction is completed, the compound of interest is isolated from the post-reaction mixture by the usual method. As needed, recrystallization, column chromatography, etc. can be employed for the purification of the compound of interest.

Production Method at Step [c]

The benzimidazole compound represented by the general formula (1) can be produced by reacting the benzimidazole compound represented by the general formula (1-1) with an oxidizing agent in an inert solvent.

Examples of the oxidizing agent used in this reaction include peroxides such as a hydrogen peroxide solution, perbenzoic acid and m-chloroperoxybenzoic acid. The amount of the oxidizing agent used is appropriately selected from the range of a 0.8- to 5-fold molar amount relative to the benzimidazole compound represented by the general formula (1-1).

The inert solvent used in this reaction may be any solvent that does not markedly inhibit the reaction, and examples include straight-chain or cyclic ethers such as diethyl ether, tetrahydrofuran and dioxane; aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. One of these inert solvents may be used alone, and also two or more of them may be used as a mixture.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method 2

[Chem. 3]

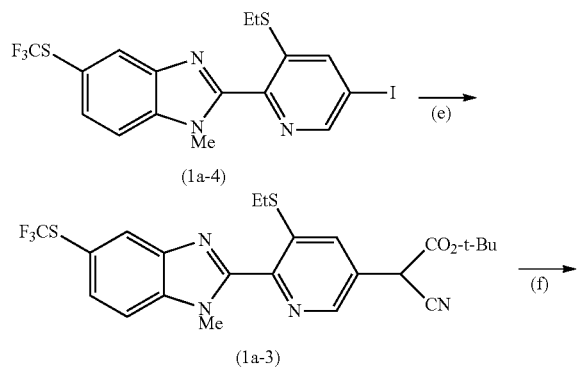

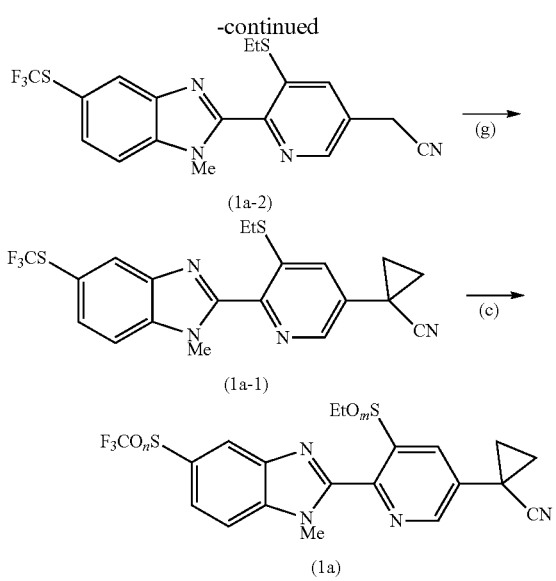

In the formula, m is as defined above, and n represents an integer of 0, 1, or 2.

Production Method at Step [e]

The benzimidazole compound represented by the general formula (1a-3) can be produced as follows. According to the method(s) described in step(s) [a] and/or [b], an iodopyridine carboxylic acid produced as described in WO 2016/104746 is reacted with a diamino compound produced as described in WO 2015/198859 to yield the benzimidazole compound represented by the general formula (1a-4). The benzimidazole compound represented by the general formula (1a-4) is coupled with a cyanoacetic acid ester as described in the literature (WO 2012/020130; and Organic & Biomolecular Chemistry, 11 (47), 8171-8174; 2013) in the presence of a metal catalyst and a base in an inert solvent to yield the desired compound.

Production Method at Step [f]

The benzimidazole compound represented by the general formula (1a-2) can be produced by hydrolysis of the benzimidazole compound represented by the general formula (1a-3) under acidic conditions and subsequent decarboxylation.

The inert solvent used in this reaction may be any solvent that does not markedly inhibit the progress of the reaction, and examples include aromatic hydrocarbons such as benzene, toluene and xylene; halogenated aliphatic hydrocarbons such as methylene chloride, chloroform and carbon tetrachloride; and halogenated aromatic hydrocarbons such as chlorobenzene and dichlorobenzene. One of these inert solvents may be used alone, and also two or more of them may be used as a mixture.

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is appropriately selected from the range of a 1-fold molar amount relative to the benzimidazole compound represented by (1a-3) to the amount of the solvent.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [g]

The benzimidazole compound represented by the general formula (1a-1) can be produced from the benzimidazole compound represented by the general formula (1a-2) according to the method described in the literature (WO 2014/113485; and Journal of Medicinal Chemistry, 57 (7), 2963-2988; 2014).

Production Method at Step [c]

The benzimidazole compound represented by the general formula (1a) can be produced from the benzimidazole compound represented by the general formula (1a-1) as described in the step [c] of Production Method 1.

The compound represented by the general formula (2), which is an intermediate in the course of the production of the compound of the present invention, can be produced by the following method.

Production Method of Intermediate (2a)

[Chem. 4]

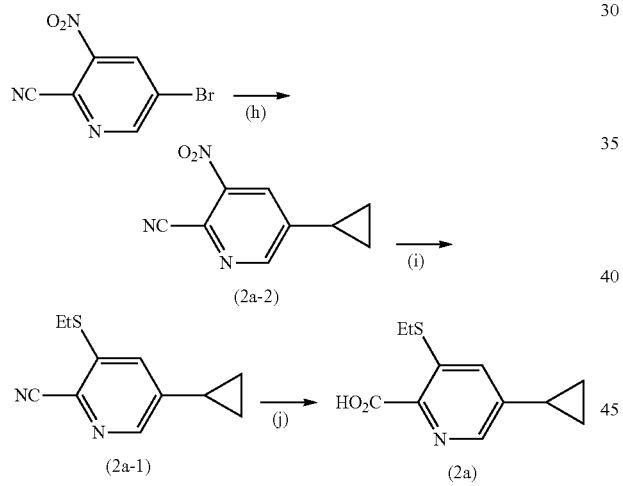

Production Method at Step [h]

The compound represented by the general formula (2a-2) can be produced by cross-coupling of a commercially available 3-nitro-2-cyano-5-bromopyridine with cyclopropylboronic acid according to the method described in the literature (Journal of Synthetic Organic Chemistry, Japan, vol. 69, No. 7, 2011; Chem. Rev. 2011, 4475; and WO 2013/018928) in the presence of a metal catalyst and a base in an inert solvent.

Production Method at Step [i]

The compound represented by the general formula (2a-1) can be produced by reacting the nitropyridine represented by the general formula (2a-2) with sodium ethanethiolate in an inert solvent.

The inert solvent used in this reaction may be any solvent that does not markedly inhibit the progress of the reaction, and examples include aromatic hydrocarbons such as benzene, toluene and xylene; halogenated aromatic hydrocarbons such as chlorobenzene and dichlorobenzene; straight-chain or cyclic ethers such as diethyl ether, methyl tert-butyl ether, dioxane and tetrahydrofuran; and polar solvents such as dimethyl sulfoxide, 1,3-dimethyl-2-imidazolidinone and water. One of these inert solvents may be used alone, and also two or more of them may be used as a mixture.

Since this reaction is an equimolar reaction of the reactants, the nitropyridine represented by the general formula (2a-2) and sodium ethanethiolate are used basically in equimolar amounts, but either of them may be used in an excess amount. The reaction temperature may be in the range of −10° C. to the boiling point of the inert solvent used. The reaction time varies with the reaction scale and the reaction temperature, but is basically in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [j]

The compound represented by the general formula (2a) can be produced from the cyanopyridine represented by the general formula (2a-1) according to the method described in J. C. S. C 1966, 840; and Chem. Pharm. Bull., 17, 1564, 1969.

Production Method of Intermediate (3)

The compound represented by the general formula (3) is a known compound and can be produced, for example, by the method described in WO 2015/198859.

Specific examples of the compound of the present invention are shown below. In the present disclosure including the following tables etc., Et stands for an ethyl group, Me stands for a methyl group, MeO stands for a methoxy group, and CN stands for a cyano group. Shown in the column of "Physical property value" is a melting point (° C.) or "NMR". NMR data are shown in different tables.

[Chem. 5]

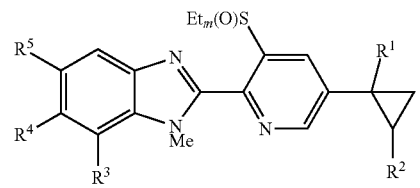

TABLE 1

| Compound No. | $R^1$ | $R^2$ | $R^3$ | $R^4$ | $R^5$ | m | Physical property value |
|---|---|---|---|---|---|---|---|
| 1-1 | H | H | H | H | $SCF_3$ | 0 | 134-136 |
| 1-2 | H | H | H | H | $SCF_3$ | 1 | 185-186 |
| 1-3 | H | H | H | H | $SCF_3$ | 2 | 111-113 |
| 1-4 | H | H | H | H | $SOCF_3$ | 2 | NMR |
| 1-5 | H | H | H | H | $SO_2CF_3$ | 2 | NMR |
| 1-6 | CN | H | H | H | $SCF_3$ | 0 | 143-145 |
| 1-7 | CN | H | H | H | $SCF_3$ | 1 | 182-184 |
| 1-8 | CN | H | H | H | $SCF_3$ | 2 | 175-177 |
| 1-9 | CN | H | H | H | $SOCF_3$ | 2 | 165-166 |
| 1-10 | CN | H | H | H | $SO_2CF_3$ | 2 | 218-219 |
| 1-11 | H | CN | H | H | $SCF_3$ | 0 | |
| 1-12 | H | CN | H | H | $SCF_3$ | 1 | |
| 1-13 | H | CN | H | H | $SCF_3$ | 2 | |
| 1-14 | H | CN | H | H | $SOCF_3$ | 2 | |

TABLE 1-continued

| Compound No. | R¹ | R² | R³ | R⁴ | R⁵ | m | Physical property value |
|---|---|---|---|---|---|---|---|
| 1-15 | H | CN | H | H | SO₂CF₃ | 2 | |
| 1-16 | H | H | H | H | CF(CF₃)₂ | 0 | 118-120 |
| 1-17 | H | H | H | H | CF(CF₃)₂ | 1 | |
| 1-18 | H | H | H | H | CF(CF₃)₂ | 2 | 156-158 |
| 1-19 | H | H | H | F | CF(CF₃)₂ | 0 | |
| 1-20 | H | H | H | F | CF(CF₃)₂ | 1 | 140-143 |
| 1-21 | H | H | H | F | CF(CF₃)₂ | 2 | 159-160 |
| 1-22 | H | H | H | H | CF₂CF₃ | 0 | |
| 1-23 | H | H | H | H | CF₂CF₃ | 1 | |
| 1-24 | H | H | H | H | CF₂CF₃ | 2 | |
| 1-25 | H | H | H | H | OCF₃ | 0 | NMR |

TABLE 2

| Compound No. | R¹ | R² | R³ | R⁴ | R⁵ | m | Physical property value |
|---|---|---|---|---|---|---|---|
| 1-26 | H | H | H | H | OCF₃ | 1 | |
| 1-27 | H | H | H | H | OCF₃ | 2 | 112-114 |
| 1-25' | H | H | H | H | OCH₂CF₃ | 0 | |
| 1-26' | H | H | H | H | OCH₂CF₃ | 1 | |
| 1-27' | H | H | H | H | OCH₂CF₃ | 2 | |
| 1-28 | CH=NOCH₂CF₃ | H | H | H | SCF₃ | 0 | |
| 1-29 | CH=NOCH₂CF₃ | H | H | H | SCF₃ | 1 | |
| 1-30 | CH=NOCH₂CF₃ | H | H | H | SCF₃ | 2 | |
| 1-31 | CH=NOCH₂CF₃ | H | H | H | SOCF₃ | 2 | |
| 1-32 | CH=NOCH₂CF₃ | H | H | H | SO₂CF₃ | 2 | |
| 1-33 | H | CH=NOCH₂CF₃ | H | H | SCF₃ | 0 | |
| 1-34 | H | CH=NOCH₂CF₃ | H | H | SCF₃ | 1 | |
| 1-35 | H | CH=NOCH₂CF₃ | H | H | SCF₃ | 2 | |
| 1-36 | H | CH=NOCH₂CF₃ | H | H | SOCF₃ | 2 | |
| 1-37 | H | CH=NOCH₂CF₃ | H | H | SO₂CF₃ | 2 | |
| 1-38 | H | H | Me | H | SCF₃ | 0 | |
| 1-39 | H | H | Me | H | SCF₃ | 1 | |
| 1-40 | H | H | Me | H | SCF₃ | 2 | |
| 1-41 | H | H | Me | H | SOCF₃ | 2 | |
| 1-42 | H | H | Me | H | SO₂CF₃ | 2 | |
| 1-43 | CN | H | Me | H | SCF₃ | 0 | |
| 1-44 | CN | H | Me | H | SCF₃ | 1 | |
| 1-45 | CN | H | Me | H | SCF₃ | 2 | |
| 1-46 | CN | H | Me | H | SOCF₃ | 2 | |
| 1-47 | CN | H | Me | H | SO₂CF₃ | 2 | |
| 1-48 | H | H | OMe | H | SCF₃ | 0 | |
| 1-49 | H | H | OMe | H | SCF₃ | 1 | |
| 1-50 | H | H | OMe | H | SCF₃ | 2 | |

TABLE 3

| Compound No. | R¹ | R² | R³ | R⁴ | R⁵ | m | Physical property value |
|---|---|---|---|---|---|---|---|
| 1-51 | H | H | OMe | H | SOCF₃ | 2 | |
| 1-52 | H | H | OMe | H | SO₂CF₃ | 2 | |
| 1-53 | CN | H | OMe | H | SCF₃ | 0 | |
| 1-54 | CN | H | OMe | H | SCF₃ | 1 | |
| 1-55 | CN | H | OMe | H | SCF₃ | 2 | |
| 1-56 | CN | H | OMe | H | SOCF₃ | 2 | |
| 1-57 | CN | H | OMe | H | SO₂CF₃ | 2 | |
| 1-58 | H | H | I | H | SCF₃ | 0 | |
| 1-59 | H | H | I | H | SCF₃ | 1 | |

TABLE 3-continued

| Compound No. | R¹ | R² | R³ | R⁴ | R⁵ | m | Physical property value |
|---|---|---|---|---|---|---|---|
| 1-60 | H | H | I | H | SCF₃ | 2 | |
| 1-61 | H | H | I | H | SOCF₃ | 2 | |
| 1-62 | H | H | I | H | SO₂CF₃ | 2 | |
| 1-63 | CN | H | I | H | SCF₃ | 0 | |
| 1-64 | CN | H | I | H | SCF₃ | 1 | |
| 1-65 | CN | H | I | H | SCF₃ | 2 | |
| 1-66 | CN | H | I | H | SOCF₃ | 2 | |
| 1-67 | CN | H | I | H | SO₂CF₃ | 2 | |
| 1-68 | H | H | H | SCF₃ | H | 0 | 129-131 |
| 1-69 | H | H | H | SCF₃ | H | 1 | 162-163 |
| 1-70 | H | H | H | SCF₃ | H | 2 | 118-120 |

TABLE 4

| Compound No. | R¹ | R² | R³ | R⁴ | R⁵ | m | Physical property value |
|---|---|---|---|---|---|---|---|
| 1-71 | H | H | H | H | OCF₂CHF₂ | 0 | NMR |
| 1-72 | H | H | H | H | OCF₂CHF₂ | 1 | |
| 1-73 | H | H | H | H | OCF₂CHF₂ | 2 | NMR |
| 1-74 | H | H | H | H | OCF₂CF₃ | 0 | NMR |
| 1-75 | H | H | H | H | OCF₂CF₃ | 1 | |
| 1-76 | H | H | H | H | OCF₂CF₃ | 2 | 133-134 |
| 1-77 | H | H | H | OCF₃ | H | 0 | NMR |
| 1-78 | H | H | H | OCF₃ | H | 1 | 133-134 |
| 1-79 | H | H | H | OCF₃ | H | 2 | 129-131 |

TABLE 4-continued

| Compound No. | R¹ | R² | R³ | R⁴ | R⁵ | m | Physical property value |
|---|---|---|---|---|---|---|---|
| 1-80 | H | H | H | OCF₂CHF₂ | H | 0 | NMR |
| 1-81 | H | H | H | OCF₂CHF₂ | H | 1 | |
| 1-82 | H | H | H | OCF₂CHF₂ | H | 2 | NMR |

TABLE 5

| Compound No. | R¹ | R² | R³ | R⁴ | R⁵ | m | Physical property value |
|---|---|---|---|---|---|---|---|
| 1-83 | CN | H | H | H | OCF₃ | 0 | NMR |
| 1-84 | CN | H | H | H | OCF₃ | 1 | |
| 1-85 | CN | H | H | H | OCF₃ | 2 | NMR |

TABLE 6

| Compound No. | ¹H-NMR Data (CDCl₃) |
|---|---|
| 1-4 | 8.73(d, 1H), 8.25(s, 1H), 8.06(d, 1H), 7.76(d, 1H), 7.64(d, 1H), 3.82-3.76(m, 5H), 2.15-2.08(m, 1H), 1.33(t, 3H), 1.27-1.25(m, 2H), 0.98-0.94(m, 2H) |
| 1-5 | 8.73(d, 1H), 8.50(s, 1H), 8.06(d, 1H), 8.00(d, 1H), 7.66(d, 1H), 3.82-3.75(m, 5H), 2.15-2.08(m, 1H), 1.34(t, 3H), 1.29-1.26(m, 2H), 0.97-0.94(m, 2H) |

TABLE 7

| Compound No. | ¹H-NMR Data (CDCl₃) |
|---|---|
| 1-25 | 8.25(d, 1H), 7.74(s, 1H), 7.38(d, 1H), 7.36(d, 1H), 7.22(d, 1H), 3.88(s,3H), 2.91(dd, 2H), 2.08-1.95(dd, 2H), 1.13(t, 3H), 1.16-1.11(dd, 2H), 0.86-0.82(dd, 2H) |
| 1-71 | 8.25(d, 1H), 7.72(d, 1H), 7.38(d, 1H), 7.36(s, 1H), 7.21(dd, 1H), 6.09-5.81(dt, 1H), 3.87(s, 3H), 2.91(dd, 2H), 2.02-1.95(m, 1H), 1.31(t,3H), 1.16-1.11(m, 2H), 0.86-0.81(m, 2H) |
| 1-73 | 8.71(d, 1H), 8.04(d, 1H), 7.62(d, 1H), 7.40(s, 1H), 7.24(dd, 1H), 6.08-5.82(dt, 1H), 3.80(dd, 2H), 3.73(s, 3H), 2.12-2.08(m, 1H), 1.32(t,3H), 1.28-1.23(m, 2H), 0.96-0.92(m, 2H) |
| 1-74 | 8.26(d, 1H), 7.73(d, 1H), 7.39(d, 1H), 7.36(d, 1H), 7.20(dd, 1H), 3.88(s,3H), 2.91(dd, 2H), 1.99-1.95(m, 1H), 1.32(t, 3H), 1.16-1.11(m, 2H), 0.86-0.82(m, 2H) |
| 1-77 | 8.25(d, 1H), 7.84(d, 1H), 7.36(d, 1H), 7.27(d, 1H), 7.18(dd, 1H), 3.87(s,3H), 2.91(dd, 2H), 1.99-1.94(m, 1H), 1.31(t, 3H), 1.16-1.11(m, 2H),0.85-0.81(m, 2H) |
| 1-80 | 8.25(d, 1H), 7.83(d, 1H), 7.36(d, 1H), 7.27(s, 1H), 7.16(dd, 1H), 6.09-5.82(dt, 1H), 3.85(s, 3H), 2.91(dd, 2H), 2.01-1.96(m, 1H), 1.31(t,3H), 1.16-1.11(m, 2H), 0.86-0.81(m, 2H) |
| 1-82 | 8.71(d, 1H), 8.05(d, 1H), 7.73(d, 1H), 7.29(s, 1H), 7.17(dd, 1H), 6.11-5.82(dt, 1H), 3.80(dd, 2H), 3.71(s, 3H), 2.12-2.06(m, 1H), 1.32(t,3H), 1.28-1.22(m, 2H), 0.97-0.92(m, 2H) |

TABLE 8

| Compound No. | ¹H-NMR Data (CDCl₃) |
|---|---|
| 1-83 | 8.31(d, 1H), 7.76(s, 1H), 7.71(d, 1H), 7.40(d, 1H), 7.25(d, 3.91(s,3H), 2.98(dd, 2H), 1.89(dd, 2H), 1.56(dd, 2H), 1.36(t, 3H) |

TABLE 8-continued

| Compound No. | ¹H-NMR Data (CDCl₃) |
|---|---|
| 1-85 | 9.03(s, 1H), 8.22(s, 1H), 7.64(d, 1H), 7.43(d, 1H), 7.28(d, 1H), 3.91(dd,2H), 3.77(s, 3H), 2.04-2.00(m, 2H), 1.67-1.64(m, 2H), 1.35(t, 3H) |

The agricultural and horticultural insecticide comprising the benzimidazole compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, other pests such as nematodes, etc.

Specific examples of the pests, nematodes, etc. include the following:

the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura,* a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata,*

*Bambalina* sp., *Carposina niponensis, Conogethes punctiferalis, Synanthedon* sp., *Lyonetia clerkella, Papilio helenus, Colias erate poliographus, Phalera flavescens,* the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anoinis flava, Pectinophora gossypiella, Notarcha derogata, Diaphania indica, Heliothis virescens* and *Earias cupreoviridis;* the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anononeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca* spp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Patrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii;* the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis;* the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans,* the species of the family Phoridae such as *Megaselia spiracularis, Clogmnia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dor-*

*salis, Dacus tsuneonis, Sitodiplosis mosellana, Meromuza nigriventris, Anastrepha ludens* and *Rhagoletis pomonella*;

the species of the order Hymenoptera such as *Pristomyrmex pungens*, the species of the family Bethylidae, *Monomorium pharaonis, Pheidole noda, Athalia rosae, Dryocosmus kuriphilus, Formica fusca japonica*, the species of the subfamily Vespinae, *Athalia infumata infumata, Arge pagana, Athalia japonica, Acromyrmex* spp., *Solenopsis* spp., *Arge mali* and *Ochetellus glaber*;

the species of the order Orthoptera such as *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma*;

the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Frankliniella occidentalis, Thrips palmi, Frankliniella lilivora* and *Liothrips vaneeckei*;

the species of the order Acari such as *Leptotrombidium akamushi, Tetranychus ludeni, Dermacentor variabilis, Tetranychus truncatus, Ornithonyssus bacoti, Demodex canis, Tetranychus viennensis, Tetranychus kanzawai*, the species of the family Ixodidae such as *Rhipicephalus sanguineus, Cheyletus malaccensis, Tyrophagus putrescentiae, Dermatophagoides farinae, Latrodectus hasseltii, Dermacentor taiwanensis, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus*;

the species of the order Blattodea such as *Periplaneta fuliginosa, Blattella germanica, Blatta orientalis, Periplaneta brunnea, Blattella lituricollis, Periplaneta japonica* and *Periplaneta americana*;

the species of the order Siphonaptera such as *Pulex irritans, Ctenocephalides felis* and *Ceratophyllus gallinae*;

the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans*; and the species of the phylum Mollusca such as *Pomacea canaliculata, Achatina fulica, Meghimatium bilineatum, Lehmannina valentiana, Limax flavus* and *Acusta despecta sieboldiana*.

In addition, the agricultural and horticultural insecticide of the present invention has a strong insecticidal effect on *Tuta absoluta* as well.

Further, animal-parasitic mites and ticks which live in the interior of or on the exterior of animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanensis*; *Dermanyssus gallinae*; the species of the genus *Ornithonyssus* such as *Ornithonyssus sylviarum* and *Ornithonyssus bursa*; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus*.

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*.

Other target pests include the following endoparasites:
from the order Enoplida, for example, *Trichuris* spp. (whipworms), *Capillaria* spp. (hairworms), *Trichomosoides* spp., *Trichinella* spp. (roundworms), etc.;
from the order Rhabditida, for example, *Micronema* spp., *Strongyloides* spp., etc.;
from the order Strongylida, for example, *Strongylus* spp. (strongyles), *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp. (nodule worms), *Chabertia* spp., *Stephanurus* spp. (*Stephanurus dentatus*), *Ancylostoma* spp. (*Ancylostoma duodenale*), *Uncinaria* spp., *Bunostomum* spp., *Globocephalus* spp., *Syngamus* spp., *Cyathostoma* spp., *Metastrongylus* spp. (lungworms), *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Angiostrongylus* spp. (*Angiostrongylus cantonensis*), *Aelurostrongylus* spp., *Filaroides* spp., *Parafilaroides* spp.,

*Trichostrongylus* spp. (*trichostrongyles*), *Haemonchus* spp. (*Haemonchus contortus*), *Ostertagia* spp., *Marshallagia* spp., *Cooperia* spp., *Nematodirus* spp. (*nematodes*), *Hyostrongylus* spp., *Obeliscoides* spp., *Amidostomum* spp., *Ollulanus* spp., etc.;

from the order Oxyurida, for example, *Oxyuris* spp. (*Oxyuris* equi), *Enterobius* spp. (pinworms), *Passalurus* spp., *Syphacia* spp., *Aspiculuris* spp., *Heterakis* spp., etc.;

from the order *Ascaridia*, for example, *Ascaris* spp. (ascarids), *Toxascaris* spp., *Toxocara* spp. (*Toxocara canis*), *Parascaris* spp. (*Parascaris equorum*), *Anisakis* spp., *Ascaridia* spp., etc.;

from the order Spirurida, for example, *Gnathostoma* spp., *Physaloptera* spp., *Thelazia* spp., *Gongylonema* spp., *Habronema* spp., *Parabronema* spp., *Draschia* spp., *Dracunculus* spp. (*Dracunculus medinensis*), etc.;

from the order Filariida, for example, *Stephanofilaria* spp., *Parafilaria* spp., *Setaria* spp., *Loa* spp., *Dirofilaria* spp. (*Dirofilaria immitis*), *Litomosoides* spp., *Brugia* spp., *Wuchereria* spp., *Onchocerca* spp., etc.; and from the order Gigantorhynchida, for example, *Filicollis* spp., *Moniliformis* spp., *Macracanthorhynchus* spp., *Prosthenorchis* spp., etc.

The endoparasite control agent comprising the benzimidazole compound represented by the general formula (1) of the present invention or a salt thereof as an active ingredient is effective against not only parasites that live in the body of an intermediate or final host, but also parasites that live in the body of a reservoir host. The compound represented by the general formula (1) of the present invention is effective at every developmental stage of parasites. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound is effective against their eggs, larvae and adults. The compound of the present invention is capable of not only combating parasites in the living body, but also even preventing parasitic infection by application to the environment as a route of infection. For example, soil-borne infection, i.e., infection from soil of crop fields and parks; percutaneous infection from water in rivers, lakes, marshes, paddy fields, etc.; oral infection from feces of animals such as dogs and cats; oral infection from saltwater fish, freshwater fish, crustaceans, shellfish, raw meat of domestic animals, etc.; infection from mosquitoes, gadflies, flies, cockroaches, mites and ticks, fleas, lice, assassin bugs, trombiculid mites, etc.; and the like can be prevented from occurring.

The endoparasite control agent of the present invention can be administered as a pharmaceutical for treatment or prevention of parasitosis in humans and animals of non-human mammalian or avian species. The mode of administration may be oral or parenteral administration. In the case of oral administration, the endoparasite control agent of the present invention can be administered, for example, as a capsule, a tablet, a pill, a powder, a granule, a fine granule, a powder, a syrup, an enteric-coated preparation, a suspension or a paste, or after blended in a liquid drink or feed for animals. In the case of parenteral administration, the endoparasite control agent of the present invention can be administered in a dosage form which allows sustained mucosal or percutaneous absorption, for example, an injection, an infusion, a suppository, an emulsion, a suspension, a drop, an ointment, a cream, a solution, a lotion, a spray, an aerosol, a cataplasm, or a tape.

In the case where the endoparasite control agent of the present invention is used as a pharmaceutical for humans and animals of non-human mammalian or avian species, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight. Such a dose may be given as a single dose or in divided doses.

The concentration of the active ingredient in the endoparasite control agent of the present invention is generally about 0.001 to 100% by mass, preferably about 0.001 to 99% by mass, and more preferably about 0.005 to 20% by mass. The endoparasite control agent of the present invention may be a composition that can be directly administered, or a highly concentrated composition that needs to be diluted to a suitable concentration before use.

The endoparasite control agent of the present invention can be used in combination with any existing endoparasite control agent for the purpose of reinforcing or complementing its effect. In such a combined use, two or more active ingredients may be mixed and formulated into a single preparation before administration, or two or more different preparations may be administered separately.

The agricultural and horticultural insecticide comprising the benzimidazole compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide utilizes so-called penetration and translocation. That is, nursery soil, soil in transplanting holes, plant foot, irrigation water, cultivation water in hydroponics, or the like is treated with the agricultural and horticultural insecticide to allow crops, ornamental flowering plants, etc. to absorb the compound of the present invention through the roots via soil or otherwise.

Examples of useful plants to which the agricultural and horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives, Welsh onions, etc.), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control target pests, the agricultural and horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of an agrochemical and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated with the agricultural and horticultural insecticide of the present invention in the period of seeding to seedling culture. In the case of plants of which the seeds are directly shown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared by the usual method for preparing agrochemical formulations.

That is, the benzimidazole compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated aliphatic hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, polyoxyethylene ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticide of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticide).

The application rate of the agricultural and horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticide of the present invention can be used after mixed with other agricultural and horticultural insecticides, acaricides, nematicides, microbicides, biopesticides and/or the like. Further, the agricultural and horticultural insecticide can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensis israelensis, Bacillus thuringiensis japonen-* sis, *Bacillus thuringiensis kurstaki* and *Bacillus thuringiensis tenebrionis*, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-lsopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrinethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) andentomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor, avirulent Erwinia carotovora* and *Bacillus subtilis*; and biopesticides used as a herbicide, such as *Xanthomonas campestris*. Such a combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-'0-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

The compound of the present invention or a salt thereof is also suitable for the disinfection of parasites that live in the interior of or on the exterior of animals such as humans, domestic animals and pets. The animal may be a non-human animal.

The present invention also includes an animal ectoparasite control agent comprising the compound of the present invention or a salt thereof as an active ingredient; and a method for controlling animal ectoparasites, comprising treating animal ectoparasites with the animal ectoparasite control agent. The compound of the present invention can be used by spot-on or pour-on application usually to one site or two sites on the skin of an animal such as a cat or a dog. The application area is usually 5 to 10 $cm^2$. Once applied, the compound of the present invention preferably diffuses throughout the animal's body and then dries without crystallization or changes in visual appearance or texture. The preferable amount of the compound used is selected from the range of 0.1 to 10 mL according to the weight of the animal, and in particular, is about 0.5 to 1 mL for a cat and about 0.3 to 3 mL for a dog.

The ectoparasite control agent of the present invention is effective against, for example, the following animal ectoparasites. Siphonaptera parasites include the species of the genus *Pulex* such as *Pulex irritans*; the species of the genus *Ctenocephalides* such as *Ctenocephalides felis* and *Ctenocephalides canis*; the species of the genus *Xenopsylla* such as *Xenopsylla cheopis*; the species of the genus *Tunga* such as *Tunga penetrans*; the species of the genus *Echidnophaga* such as *Echidnophaga gallinacea*; and the species of the genus *Nosopsyllus* such as *Nosopsyllus fasciatus*.

Siphunculata parasites include the species of the genus *Pediculus* such as *Pediculus humanus capitis*; the species of the genus *Pthirus* such as *Pthirus pubis*; the species of the genus *Haematopinus* such as *Haematopinus eurysternus* and *Haematopinus suis*; the species of the genus *Damalinia* such as *Damalinia ovis* and *Damalinia bovis*; the species of the genus *Linognathus* such as *Linognathus vituli* and *Linognathus ovillus* (parasitic on the trunk of a sheep's body); and the species of the genus *Solenopotes* such as *Solenopotes capillatus*.

Mallophaga parasites include the species of the genus *Menopon* such as *Menopon gallinae; Trimenopon* spp.; *Trinoton* spp.; the species of the genus *Trichodectes* such as *Trichodectes canis*; the species of the genus *Felicola* such as *Felicola subrostratus*; the species of the genus *Bovicola* such as *Bovicola bovis*; the species of the genus *Menacanthus* such as *Menacanthus stramineus; Werneckiella* spp.; and *Lepikentron* spp.

Hemiptera parasites include the species of the genus *Cimex* such as *Cimex lectularius* and *Cimex hemipterus*; the species of the genus *Reduvius* such as *Reduvius senilis*; the species of the genus *Arilus* such as *Arilus critatus*; the species of the genus *Rhodnius* such as *Rhodnius prolixus*; the species of the genus *Triatoma* such as *Triatoma rubrofasciata*; and *Panstrongylus* spp.

Acarina parasites include the species of the genus *Amblyomma* such as *Amblyomma americanum* and *Amblyomma maculatum*; the species of the genus *Boophilus* such as *Boophilus microplus* and *Boophilus annulatus*; the species of the genus *Dermacentor* such as *Dermacentor variabilis, Dermacentor taiwanensis* and *Dermacentor andersoni*; the species of the genus *Haemaphysalis* such as *Haemaphysalis longicornis, Haemaphysalis flava* and *Haemaphysalis campanulata*; the species of the genus *Ixodes* such as *Ixodes ovatus, Ixodes persulcatus, Ixodes scapularis, Ixodes pacificus* and *Ixodes holocyclus*; the species of the genus *Rhipicephalus* such as *Rhipicephalus sanguineus* and *Rhipicephalus appendiculatus*; the species of the genus *Argas* such as *Argas persicus*; the species of the genus *Ornithodoros* such as *Ornithodoros hermsi* and *Ornithodoros turicata*; the species of the genus *Psoroptes* such as *Psoroptes ovis* and *Psoroptes equi*; the species of the genus *Knemidocoptes* such as *Knemidocoptes mutans*; the species of the genus *Notoedres* such as *Notoedres cati* and *Notoedres muris*; the species of the genus *Sarcoptes* such as *Sarcoptes scabiei*; the species of the genus *Otodectes* such as *Otodectes cynotis*; the species of the genus *Listrophorus* such as *Listrophorus gibbus; Chorioptes* spp.; *Hypodectes* spp.; *Pterolichus* spp.; *Cytodites* spp.; *Laminosioptes* spp.; the species of the genus *Dermanyssus* such as *Dermanyssus gallinae*; the species of the genus *Ornithonyssus* such as *Ornithonyssus sylviarum* and *Ornithonyssus bacoti*; the species of the genus *Varroa* such as *Varroa jacobsoni*; the species of the genus *Cheyletiella* such as *Cheyletiella yasguri* and *Cheyletiella blakei; Ornithocheyletia* spp.; the species of the genus *Demodex* such as *Demodex canis* and *Demodex cati; Myobia* spp.; *Psorergates* spp.; and the species of the genus *Trombicula* such as *Trombicula akamushi, Trombicula pallida* and *Trombicula scutellaris*. Preferred are Siphonaptera parasites, Siphunculata parasites and Acarina parasites.

The animals to which the ectoparasite control agent of the present invention is administrable can be host animals for the above-mentioned animal ectoparasites. Such animals are usually homeotherms and poikilotherms which are bred as domestic animals or pets. Such homeotherms include mammals such as cattle, buffalos, sheep, goats, pigs, camels, deer, fallow deer, reindeer, horses, donkeys, dogs, cats, rabbits, ferrets, mice, rats, hamsters, squirrels and monkeys; fur-bearing animals such as minks, chinchillas and raccoons; and birds such as chickens, geese, turkeys, domestic ducks, pigeons, parrots and quails. The above-mentioned poikilotherms include reptiles such as tortoises, sea turtles, pond sliders, Japanese pond turtles, lizards, iguanas, chameleons, geckos, pythons, colubrid snakes and cobras. Preferred are homeotherms, and more preferred are mammals such as dogs, cats, cattle, horses, pigs, sheep and goats.

Since the control agent of the present invention is unlikely to damage or impact natural enemies (nontarget organisms), two or more insect pest control methods etc. can be rationally combined for use.

Examples of the nontarget organism include natural predators such as *Phytoseiulus persimilis, Neoseiulus californicus, Amblyseius swirskii* Athias-Henriot, *Neoseiulus womersleyi*, and *Typhlodromus vulgaris*; and useful insects such as honey bees, western honey bees (*Apis mellifera*), bumblebees, buff-tailed bumblebees (*Bombus terrestris*), horned-face bees (*Osmia cornifrons*), and domestic silkmoths (*Bombyx mori*).

Hereinafter, the production examples of representative compounds of the present invention and their intermediates will be described in more detail, but the present invention is not limited only to these examples.

EXAMPLES

Reference Example 1

Production Example of Intermediate (2)

Production Method of
3-ethylthio-2-cyano-5-cyclopropylpyridine

[Chem. 6]

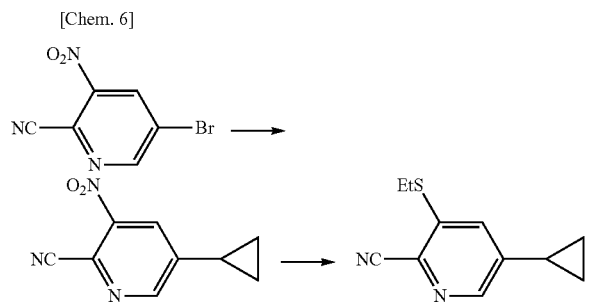

A commercial 3-nitro-2-cyano-5-bromopyridine (8 g, 35 mmol), cyclopropylboronic acid (3.6 g, 1.2 Eq), potassium carbonate (14.5 g, 3 Eq), palladium acetate (79 mg, 1 mol %), and SPhos (2-dicyclohexylphosphino-2',2',6'-dimethoxybiphenyl) (288 mg, 1 mol %) were dissolved in a mixed solvent of toluene (140 mL) and water (14 mL), and the mixture was reacted at 80° C. under an argon atmosphere for 4 hours. After cooling, water (140 mL) was added for liquid-liquid partition. The organic layer was washed with a saturated aqueous potassium carbonate solution (50 mL).

Tetraoctyl ammonium bromide (1.0 g, 5 mol %) was added to the organic layer, and the mixture was cooled to 5° C. or below. To this, an aqueous solution prepared by diluting an 80% aqueous NaSEt solution (4.0 g, 1.1 Eq) with water (20 mL) was added dropwise while the temperature was kept at 10° C. or below. After dropwise addition, the reaction was further continued for 1 hour. After liquid-liquid partition, the organic layer was washed with a saturated aqueous potassium carbonate solution (50 mL), dried over anhydrous sodium sulfate, and concentrated to give 10 g of the desired compound. This product was used in the subsequent reaction without purification.

Reference Example 2

Production Method of
3-ethylthio-5-cyclopropylpyridine-2-carboxylic acid

[Chem. 7]

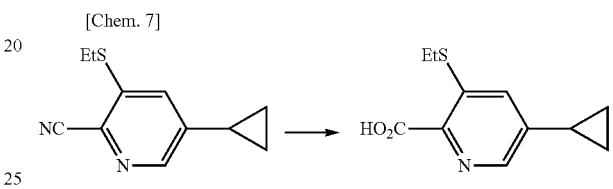

The 3-ethylthio-2-cyano-5-cyclopropylpyridine (10 g) obtained in the previous step was dissolved in ethanol (35 mL), and a 30% aqueous NaOH solution (49 g) was added. The mixture was reacted at room temperature for 3 hours and subsequently refluxed for 2 hours. After cooling, toluene (140 mL) and water (140 mL) were added for liquid-liquid partition. To the aqueous layer, concentrated hydrochloric acid (30 mL) was added dropwise at 25° C. or below. After extraction with ethyl acetate (140 mL), the organic layer was dried over anhydrous sodium sulfate and concentrated to give 3-ethylthio-5-cyclopropylpyridine-2-carboxylic acid (5.2 g, 67% (two steps)).

$^1$H-NMR; 8.01 (d, 1H), 7.31 (d, 1H), 2.95 (q, 2H), 2.00-1.94 (m, 1H), 1.42 (t, 3H), 1.21-1.16 (m, 2H), 0.87-0.84 (m, 2H)

Example 1

Production method of 2-(3-ethylthio-5-cyclopropylpyridin-2-yl)-1-methyl-5-(trifluoromethylthio)benzimidazole (compound number 1-1)

[Chem. 8]

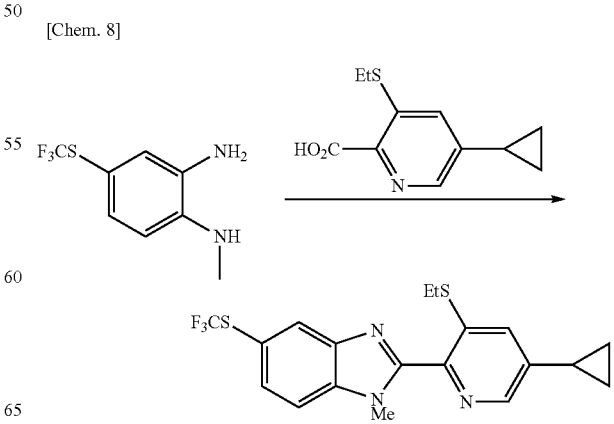

The 3-ethylthio-5-cyclopropylpyridine-2-carboxylic acid (450 mg) obtained in the previous step and 2-amino-1-methyl-4-trifluoromethylthioaniline (349 mg), which was produced as described in WO 2015/198859, were dissolved in THF (tetrahydrofuran) (4 mL). To this, triethylamine (1 mL) and 1-methyl-2-chloropyridinium iodide (1.1 g) were added successively. The reaction mixture was stirred at room temperature for 30 minutes, and ethyl acetate and water were added. The aqueous layer was extracted with ethyl acetate, and the combined organic layer was dried over anhydrous sodium sulfate and concentrated. The residue was dissolved in NMP (N-methylpyrrolidone) (5 mL), p-toluenesulfonic acid (500 mg) was added, and the mixture was reacted at 150° C. for 2 hours. After cooling, ethyl acetate extraction was performed, and the organic layer was dried and concentrated. The residue was subjected to column chromatography to give the desired compound (85 mg).

Example 2

Production Method of 2-(3-ethylsulfinyl-5-cyclopropylpyridin-2-yl)-1-methyl-5-(trifluoromethylthio)benzimidazole (compound number 1-2) and 2-(3-ethylsulfonyl-5-cyclopropylpyridin-2-yl)-1-methyl-5-(trifluoromethylthio)benzimidazole (compound number 1-3)

[Chem. 9]

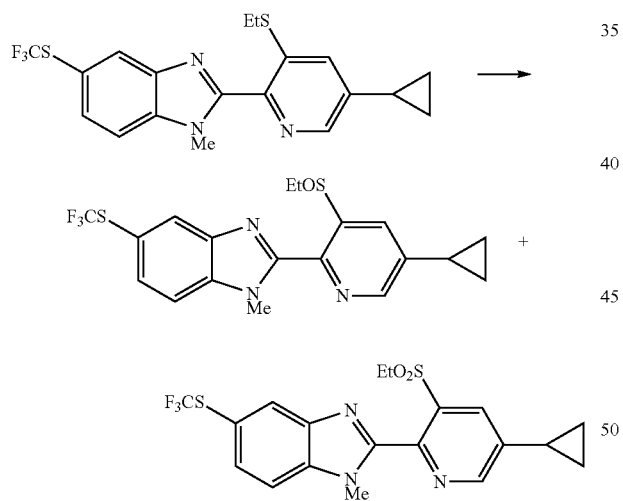

The 2-(3-ethylthio-5-cyclopropylpyridin-2-yl)-1-methyl-5-(trifluoromethylthio)benzimidazole (85 mg) obtained in the previous reaction was dissolved in ethyl acetate (2 mL). Meta-chloroperbenzoic acid (110 mg) was added, and the mixture was reacted at room temperature for 30 minutes. To this, several drops of DMSO (dimethyl sulfoxide) were added, and the mixture was concentrated and subjected to column chromatography to give 2-(3-ethylsulfinyl-5-cyclopropylpyridin-2-yl)-1-methyl-5-(trifluoromethylthio)benzimidazole (22 mg) and 2-(3-ethylsulfonyl-5-cyclopropylpyridin-2-yl)-1-methyl-5-(trifluoromethylthio)benzimidazole (66 mg).

Example 3

Production Method of 2-(3-ethylsulfonyl-5-cyclopropylpyridin-2-yl)-1-methyl-5-(trifluoromethylsulfinyl)benzimidazole (compound number 1-4) and 2-(3-ethylsulfonyl-5-cyclopropylpyridin-2-yl)-1-methyl-5-(trifluoromethylsulfonyl)benzimidazole (compound number 1-5)

[Chem. 10]

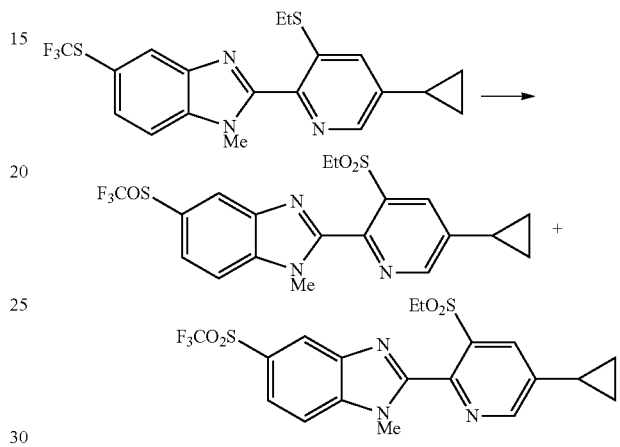

The 2-(3-ethylthio-5-cyclopropylpyridin-2-yl)-1-methyl-5-(trifluoromethylthio)benzimidazole (114 mg) produced by the production method of Example 1 was dissolved in chloroform (2 mL). Meta-chloroperbenzoic acid (259 mg) was added, and the mixture was reacted at room temperature for 1 hour. To this, several drops of DMSO were added, and the mixture was concentrated and subjected to column chromatography to give 2-(3-ethylsulfonyl-5-cyclopropylpyridin-2-yl)-1-methyl-5-(trifluoromethylsulfinyl)benzimidazole (66 mg) and 2-(3-ethylsulfonyl-5-cyclopropylpyridin-2-yl)-1-methyl-5-(trifluoromethylsulfonyl)benzimidazole (19 mg).

Reference Example 3

Production Method of 2-(3-ethylthio-5-cyanomethylpyridin-2-yl)-1-methyl-5-(trifluoromethylthio)benzimidazole

[Chem. 11]

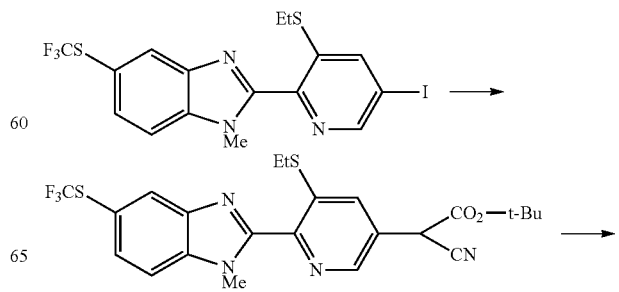

-continued

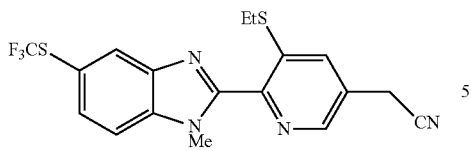

From an iodopyridine carboxylic acid produced as described in WO 2016/104746 and a diamino compound produced as described in WO 2015/198859, 2-(3-ethylthio-5-iodopyridin-2-yl)-1-methyl-5-(trifluoromethylthio)benzimidazole was produced in the same manner as in Example 1. 2-(3-Ethylthio-5-iodopyridin-2-yl)-1-methyl-5-(trifluoromethylthio)benzimidazole (502 mg), t-butyl cyanoacetate (214 mg), cesium carbonate (991 mg), and picolinic acid (124 mg) were dissolved in THF (10 mL). To this, copper iodide (97 mg) was added, and the mixture was heated at 80° C. with stirring for 4 hours. After cooling to room temperature, a 1% aqueous ammonia solution and ethyl acetate were added to the reaction mixture. The aqueous layer was extracted with ethyl acetate, and the combined organic layer was concentrated. Chloroform (5 mL) and trifluoroacetic acid (5 mL) were added to the residue, and the mixture was heated under reflux for 1 hour. The reaction mixture was concentrated, and water, an aqueous sodium bicarbonate solution, and ethyl acetate were added to the residue. The aqueous layer was extracted with ethyl acetate, and the combined organic layer was concentrated. The residue was purified by column chromatography to give the desired compound (380 mg).

Example 4

Production Method of 1-(5-ethylthio-6-(1-methyl-5-(trifluoromethylthio)benzoxazol-2-yl)pyridin-3-yl)cyclopropane carbonitrile (compound number 1-6)

[Chem. 12]

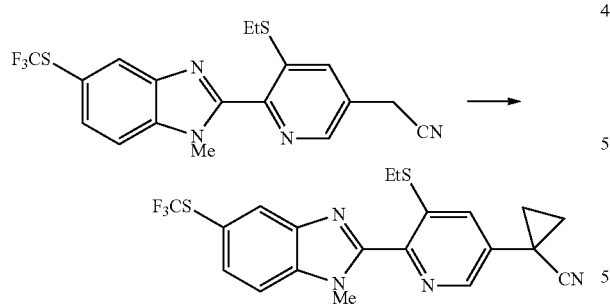

2-(3-Ethylthio-5-cyanomethylpyridin-2-yl)-1-methyl-5-trifluoromethylthiobenzimidazole (365 mg) was dissolved in DMF (5 mL), and 1,2-dibromoethane (200 mg) and sodium t-butoxide (239 mg) were added successively. The reaction mixture was stirred at room temperature for 1 hour, and water and ethyl acetate were added. The aqueous layer was extracted with ethyl acetate, and the combined organic layer was concentrated. The residue was subjected to column chromatography to give the desired compound (96 mg).

Example 5

Production Method of 1-(5-ethylsulfinyl-6-(1-methyl-5-(trifluoromethylthio)benzoxazol-2-yl)pyridin-3-yl)cyclopropane carbonitrile (compound number 1-7) and 1-(5-ethylsulfonyl-6-(1-methyl-5-(trifluoromethylthio)benzoxazol-2-yl)pyridin-3-yl)cyclopropane carbonitrile (compound number 1-8)

[Chem. 13]

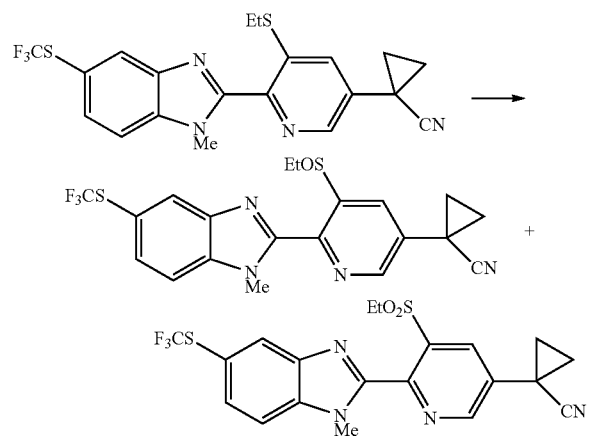

The titled compounds were synthesized in the same manner as in Example 2 from 1-(5-ethylthio-6-(1-methyl-5-(trifluoromethylthio)benzoxazol-2-yl)pyridin-3-yl)cyclopropane carbonitrile as a starting compound.

Example 6

Production Method of 1-(5-ethylsulfonyl-6-(1-methyl-5-(trifluorosulfinyl)benzoxazol-2-yl)pyridin-3-yl)cyclopropane carbonitrile (compound number 1-9) and 1-(5-ethylsulfonyl-6-(1-methyl-5-(trifluoromethylsulfonyl)benzoxazol-2-yl)pyridin-3-yl)cyclopropane carbonitrile (compound number 1-10)

[Chem. 14]

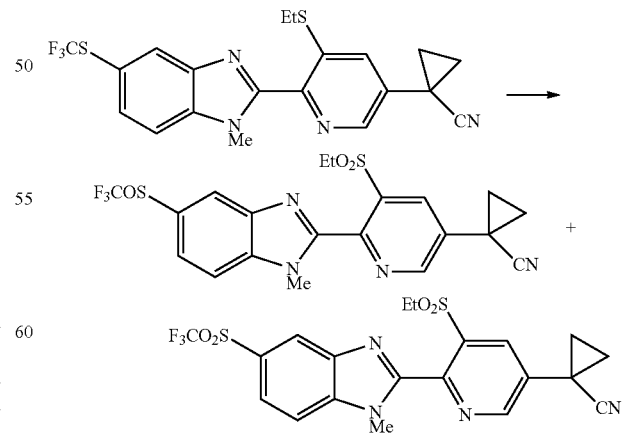

The titled compounds were synthesized in the same manner as in Example 2 from 1-(5-ethylthio-6-(1-methyl- 5-(trifluoromethylthio)benzoxazol-2-yl)pyridin)-3-yl)cyclopropane carbonitrile as a starting compound.

Example 7

Production method of 2-(5-cyclopropyl-3-ethylthiopyridin-2-yl)-1-methyl-5-trifluoromethoxybenzimidazole (compound number 1-25)

[Chem. 15]

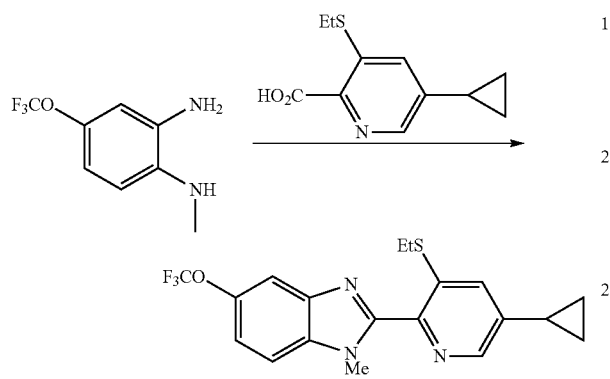

2-Amino-1-methyl-4-trifluoromethoxyaniline (420 mg) and 5-cyclopropyl-3-ethylthiopyridine-2-carboxylic acid (540 mg) were dissolved in THF (4 mL). To this, triethylamine (1 mL) and 2-chloro-1-methylpyridinium iodide (672 mg) were added successively. The reaction mixture was stirred at room temperature for 30 minutes, and ethyl acetate and water were added. The aqueous layer was extracted with ethyl acetate, and the combined organic layer was concentrated. NMP (5 mL) and p-toluenesulfonic acid (500 mg) were added to the residue, and the mixture was heated at 150° C. with stirring for 2 hours. The reaction mixture was cooled to room temperature and subjected to column chromatography to give the desired compound, i.e., 2-(5-cyclopropyl-3-ethylthiopyridin-2-yl)-1-methyl-5-trifluoromethoxybenzimidazole (863 mg).

Physical property: $^1$H-NMR (CDCl$_3$): 8.25 (d, 1H), 7.74 (s, 1H), 7.38 (d, 1H), 7.36 (d, 1H), 7.22 (d, 1H), 3.88 (s, 3H), 2.91 (dd, 2H), 2.08-1.95 (dd, 2H), 1.13 (t, 3H), 1.16-1.11 (dd, 2H), 0.86-0.82 (dd, 2H)

Example 8

Production method of 2-(5-cyclopropyl-3-ethylsulfonyl-pyridin-2-yl)-1-methyl-5-trifluoromethoxybenzimidazole (compound number 1-27)

[Chem. 16]

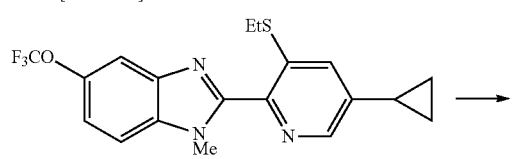

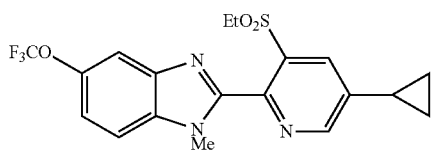

2-(5-Cyclopropyl-3-ethylthiopyridin-2-yl)-1-methyl-5-trifluoromethoxybenzimidazole (862 mg) was dissolved in ethyl acetate (2 mL), and m-chloroperbenzoic acid (1.1 g) was added. The reaction mixture was stirred at room temperature for 30 minutes and subjected to column chromatography to give the desired compound, i.e., 2-(5-cyclopropyl-3-ethylsulfonyl-pyridin-2-yl)-1-methyl-5-trifluoromethoxybenzimidazole (716 mg).

Physical property: $^1$H-NMR (CDCl$_3$): 8.71 (d, 1H), 8.05 (s, 1H), 7.63 (d, 1H), 7.41 (d, 1H), 7.24 (d, 1H), 3.79 (dd, 2H), 3.73 (s, 3H), 2.14-2.06 (dd, 2H), 1.27 (t, 3H), 1.26-1.23 (dd, 2H), 0.96-0.72 (dd, 2H)

Melting point: 112 to 114° C.

Reference Example 4

Production Method of 2-(5-iodo-3-ethylthiopyridin-2-yl)-1-methyl-5-trifluoromethoxybenzimidazole

[Chem. 17]

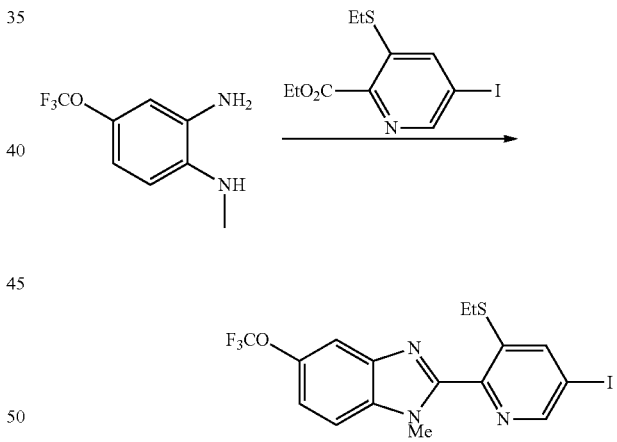

2-Amino-1-methyl-4-trifluoromethoxyaniline (467 mg) was dissolved in THF (3 mL), and triethylamine (1 mL) was added. 3-Ethylthio-5-iodopicolinic acid (840 mg) and 2-chloro-1-methylpyridinium iodide (752 mg) were added, and the mixture was reacted at room temperature overnight. Water was added, and ethyl acetate extraction was performed. The organic layer was concentrated. The residue was dissolved in NMP (5 mL), p-toluenesulfonic acid monohydrate (300 mg) was added, and the mixture was reacted at 150° C. for 2 hours. The reaction mixture was cooled to room temperature and subjected to column chromatography to give the desired compound, i.e., 2-(5-iodo-3-ethylthiopyridin-2-yl)-1-methyl-5-trifluoromethoxybenzimidazole (670 mg).

Reference Example 5

Production method of 2-(5-cyanomethyl-3-ethylthiopyridin-2-yl)-1-methyl-5-trifluoromethoxybenzimidazole

[Chem. 18]

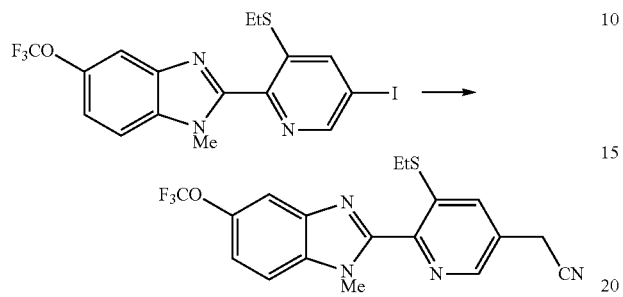

2-(5-Iodo-3-ethylthiopyridin-2-yl)-1-methyl-5-trifluoro methoxybenzimidazole (418 mg) and cyanoacetic acid t-butyl ester (185 mg) were dissolved in THF (5 mL). Cesium carbonate (850 mg) and picolinic acid (107 mg) were added. Copper iodide (83 mg) were added under an argon atmosphere, and the mixture was stirred at 80° C. for 2 hours. After cooling to room temperature, a diluted aqueous ammonia solution was added, and the mixture was stirred. 3 N hydrochloric acid was added, and ethyl acetate extraction was performed. The combined organic layer was dried over magnesium sulfate and concentrated. The residue was dissolved in chloroform (5 mL), trifluoroacetic acid (5 mL) was added, and the mixture was heated at 60° C. with stirring for 1 hour. After cooling to room temperature, toluene was added, and the mixture was concentrated. An aqueous sodium bicarbonate solution was added to the residue, and ethyl acetate extraction was performed. The organic layer was concentrated, and the residue was subjected to column chromatography to give the desired compound, i.e., 2-(5-cyanomethyl-3-ethylthiopyridin-2-yl)-1-methyl-5-trifluoromethoxybenzimidazole (168 mg).

Physical property: $^3$H-NMR (CDCl$_3$): 8.42 (s, 1H), 7.76 (s, 1H), 7.72 (d, 1H), 7.41 (d, 1H), 7.24 (dd, 1H), 3.92 (s, 3H), 3.86 (s, 2H), 2.97 (dd, 2H), 1.37 (t, 3H)

Example 9

Production Method of 2-(5-(1-cyanocyclopropyl)-3-ethylthiopyridin-2-yl)-1-methyl-5-trifluoromethoxybenzimidazole (compound number 1-83)

[Chem. 19]

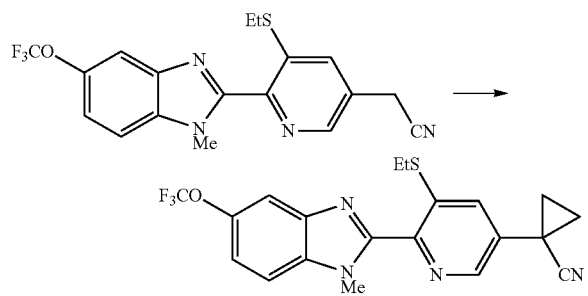

2-(5-Cyanomethyl-3-ethylthiopyridin-2-yl)-1-methyl-5-trifluoromethoxybenzimidazole (147 mg) was dissolved in DMF (2 mL), and dibromoethane (85 mg) was added. Sodium t-butoxide (101 mg) was added under ice cooling. The reaction mixture was stirred for 1 hour, water was added, and ethyl acetate extraction was performed. The organic layer was concentrated, and the residue was subjected to column chromatography to give the desired compound, i.e., 2-(5-(1-cyanocyclopropyl)-3-ethylthiopyridin-2-yl)-1-methyl-5-trifluoromethoxybenzimidazole (81 mg).

Example 10

Production Method of 2-(5-(1-cyanocyclopropyl)-3-ethylsulfonyl-pyridin-2-yl)-1-m ethyl-5-trifluoromethoxybenzimidazole (compound number 1-85)

[Chem. 20]

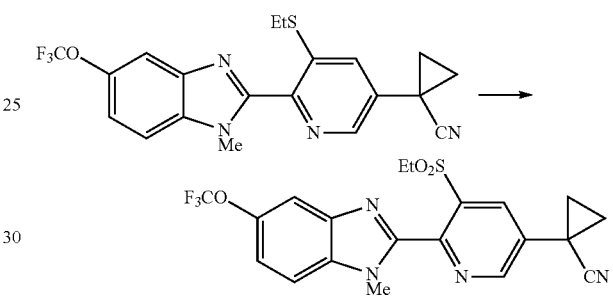

2-(5-(1-Cyanocyclopropyl)-3-ethylthiopyridin-2-yl)-1-methyl-5-trifluoromethoxybenzimidazole (76 mg) was dissolved in ethyl acetate (3 mL), and m-chloroperbenzoic acid (88 mg) was added. The reaction mixture was stirred at room temperature for 2 hours and subjected to column chromatography to give the desired compound, i.e., 2-(5-(1-cyanocyclopropyl)-3-ethylsulfonyl-pyridin-2-yl)-1-m ethyl-5-trifluoromethoxybenzimidazole (63 mg).

Hereinafter, formulation examples are shown, but the present invention is not limited thereto. In the formulation examples, "part" means part by weight.

Formulation Example 1

| Compound of the present invention | 10 parts |
| --- | --- |
| Xylene | 70 parts |
| N-methylpyrrolidone | 10 parts |
| Mixture of polyoxyethylene nonylphenyl ether and calcium alkylbenzene sulfonate (weight ratio of 1:1) | 10 parts |

The above ingredients are uniformly mixed for dissolution to give an emulsifiable concentrate formulation.

Formulation Example 2

| Compound of the present invention | 3 parts |
| --- | --- |
| Clay powder | 82 parts |
| Diatomite powder | 15 parts |

The above ingredients are uniformly mixed and then pulverized to give a dust formulation.

Formulation Example 3

| Compound of the present invention | 5 parts |
|---|---|
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| Compound of the present invention | 20 parts |
|---|---|
| Kaolin and synthetic high-dispersion silicic acid | 75 parts |
| Mixture of polyoxyethylene nonylphenyl ether and calcium alkylbenzene sulfonate (weight ratio of 1:1) | 5 parts |

The above ingredients are uniformly mixed and then pulverized to give a wettable powder formulation.

Formulation Example 5 (Emulsion)

Ten parts of the compound represented by the general formula (1) of the present invention, 6 parts of Sorpol 355S (surfactant, manufactured by Toho Chemical Industry), and 84 parts of Solvesso 150 (manufactured by Exxon) are uniformly mixed with stirring to give an emulsion formulation.

Formulation Example 6 (Ointment)

One part of the compound represented by the general formula (1) of the present invention, 50 parts of white beeswax, and 49 parts of white petrolatum are well mixed to give an ointment formulation.

Formulation Example 7 (Tablet)

Two parts of the compound represented by the general formula (1) of the present invention, 10 parts of vegetable oil (olive oil), 3 parts of crystalline cellulose, 20 parts of white carbon, and 65 parts of kaolin are well mixed and compressed into a tablet formulation.

Formulation Example 8 (Injection)

Ten parts of the compound represented by the general formula (1) of the present invention, 10 parts of propylene glycol for use as a food additive, and 80 parts of vegetable oil (corn oil) are mixed to give an injection formulation.

Five parts of the compound represented by the general formula (1) of the present invention, 20 parts of surfactant, and 75 parts of ion exchanged water are well mixed to give a solution formulation.

Hereinafter, test examples in connection with the present invention are shown, but the present invention is not limited thereto.

Test Example 1

Test for Control Efficacy on *Myzus persicae*

Chinese cabbage plants were planted in plastic pots (diameter: 8 cm, height: 8 cm), Green peach aphids (*M. persicae*) were propagated on the plants, and the number of surviving Green peach aphids in each pot was counted. The benzimidazole compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

$$\text{Control rate}=100-\{(T\times Ca)/(Ta\times C)\}\times 100 \qquad [\text{Math. 1}]$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-1, 1-2, 1-3, 1-4, 1-5, 1-6, 1-7, 1-8, 1-9, 1-10, 1-16, 1-18, 1-20, 1-21, 1-27, 1-68, 1-69, 1-70, 1-71, 1-73, 1-74, 1-76, 1-77, 1-78, 1-79, 1-80, 1-82, 1-83, and 1-85 of the present invention showed the activity level evaluated as A.

Test Example 2

Insecticidal Test on *Laodelphax striatellus*

The benzimidazole compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of *L. striatellus*, and then the glass test tubes were capped with cotton plugs. At 8 days after the inoculation, the numbers of surviving larvae and dead larvae were counted, the corrected mortality rate was calculated according to the formula shown below, and the insecticidal efficacy was evaluated according to the criteria shown below.

$$\text{Corrected mortality rate (\%)}=100\times(\text{Survival rate in a non-treatment plot}-\text{Survival rate in a treatment plot})/\text{Survival rate in a non-treatment plot} \qquad [\text{Math. 2}]$$

Corrected Mortality Rate
A: the corrected mortality rate is 100%.
B: the corrected mortality rate is 90 to 99%.
C: the corrected mortality rate is 80 to 89%.
D: the corrected mortality rate is 50 to 79%.

As a result, the compounds 1-1, 1-2, 1-3, 1-4, 1-5, 1-6, 1-7, 1-8, 1-9, 1-10, 1-16, 1-18, 1-20, 1-21, 1-27, 1-68, 1-69, 1-70, 1-71, 1-73, 1-74, 1-76, 1-77, 1-78, 1-79, 1-80, 1-82, 1-83, and 1-85 of the present invention showed the activity level evaluated as A.

Test Example 3

Insecticidal Test on *Plutella xylostella*

Adults of *P. xylostella* were released onto Chinese cabbage seedlings and allowed to lay eggs thereon. At 2 days after the release of the adults, the Chinese cabbage seedlings with laid eggs were dipped for about 30 seconds in agrochemical formulations diluted to 500 ppm, each of which contained a different benzimidazole compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal efficacy was evaluated according to the criteria of Test Example 2. This test was conducted in triplicate using 10 adults of *P. xylostella* per plot.

Corrected mortality rate (%)=100×(Number of hatched larvae in a non-treatment plot−Number of hatched larvae in a treatment plot)/Number of hatched larvae in a non-treatment plot [Math. 3]

As a result, the compounds 1-1, 1-2, 1-3, 1-4, 1-5, 1-6, 1-7, 1-8, 1-9, 1-10, 1-16, 1-18, 1-20, 1-21, 1-27, 1-68, 1-69, 1-70, 1-71, 1-73, 1-74, 1-76, 1-77, 1-78, 1-79, 1-80, 1-82, 1-83, and 1-85 of the present invention showed the activity level evaluated as A.

Test Example 4

Parasiticidal Test on *Ctenocephalides felis*

Agrochemical formulations each containing a different benzimidazole compound represented by the general formula (1) of the present invention as an active ingredient were separately diluted to a concentration of 50 ppm in bovine blood. Newly-emerged adults of *C. felis* were placed into test cages (10 adults per test cage), and the test cages were maintained at 35° C. in an artificial feeding system. At 24 hours after agrochemical treatment, the numbers of surviving and dead adults were counted, and the corrected mortality rate was calculated according to the formula shown below.

Corrected mortality rate (%)=100×(Survival rate in a negative control group−Survival rate in a treatment group)/Survival rate in a negative control group [Math. 4]

As a result, the compounds 1-3, 1-4, and 1-21 of the present invention showed parasiticidal activity with a corrected mortality rate of 90% or more.

Test Example 5

Parasiticidal Test on *Rhipicephalus sanguineus*

Agrochemical formulations each containing a different benzimidazole compound represented by the general formula (1) of the present invention as an active ingredient were separately diluted to a concentration of 100 ppm. The diluted formulations were applied dropwise onto filter paper pieces placed in separate vials. The filter paper pieces were dried. Ten nymphs of *R. sanguineus* were placed into each vial and maintained at 27° C. with 80% humidity under a 12L12D light-dark cycle (L: light time, D: dark time). At 48 hours after agrochemical treatment, the numbers of surviving and dead nymphs were counted, and the corrected mortality rate was calculated according to the formula of Math. 4.

As a result, the compounds 1-3, 1-4, and 1-79 of the present invention showed parasiticidal activity with a corrected mortality rate of 90% or more.

Test Example 6

Parasiticidal Test on *Haemonchus contortus*

Agrochemical formulations each containing a different benzimidazole compound represented by the general formula (1) of the present invention as an active ingredient were separately diluted to a concentration of 100 ppm. The diluted formulations were added to the wells of 96-well plates containing a medium for cell culture. Eggs of *H. contortus* were collected from feces of a goat and hatched in water. Twenty 1st-instar larvae of *H. contortus* were inoculated into each well, and the plates were incubated at 27° C. with 95% humidity for 96 hours. After that, larval motility was evaluated using a High Content Imaging System. The percent inhibition in motility as compared to the average motility in negative control wells was calculated by the following formula.

Percent inhibition in motility (%)=100×(Average motility in negative control wells−Average motility in treated wells)/Average motility in negative control wells [Math. 5]

As a result, the compounds 1-3, 1-4, and 1-79 of the present invention showed parasiticidal activity with a percent inhibition in motility of 50% or more.

Test Example 7

Parasiticidal Test on *Dirofilaria immitis*

Five hundred larvae of *D. immitis* were isolated by filtration from the blood collected from dogs infected with *D. immitis*, diluted in a medium for cell culture, and inoculated into the wells of 96-well plates. Agrochemical formulations each containing a different benzimidazole compound represented by the general formula (1) of the present invention as an active ingredient were separately diluted to a concentration of 50 ppm. The diluted formulations were added to the wells of the 96-well plates. Twenty L1 stage larvae (1st-instar larvae) of *D. immitis* were inoculated into each well, and the plates were incubated at 37° C. in a 5% $CO_2$ atmosphere with 95% humidity for 72 hours. After that, larval motility was evaluated using a High Content Imaging System. The percent inhibition in motility as compared to the average motility in negative control wells was calculated by the above formula.

As a result, the compounds 1-3 and 1-79 of the present invention showed parasiticidal activity with a percent inhibition in motility of 50% or more.

INDUSTRIAL APPLICABILITY

The compound of the present invention is highly effective for the control of a wide range of agricultural and horticultural pests, ectoparasites, and endoparasites and thus is useful.

The invention claimed is:

1. A benzimidazole compound represented by formula (1):

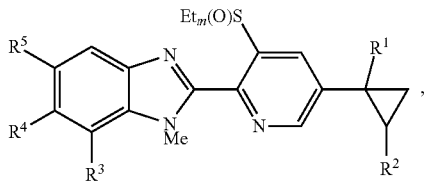

wherein
$R^1$ and $R^2$ may be the same or different, and each represent
(a1) a hydrogen atom;
(a2) a cyano group; or
(a3) a $C(R^6)=NOR^7$ group (wherein $R^6$ represents (e1) a hydrogen atom, and $R^7$ represents (f1) a halo $(C_1-C_6)$ alkyl group),
$R^3$ represents
(b1) a hydrogen atom;
(b2) a halogen atom;
(b3) a $(C_1-C_6)$ alkyl group; or
(b4) a $(C_1-C_6)$ alkoxy group,
$R^4$ represents
(c1) a hydrogen atom;
(c2) a halogen atom;
(c3) a halo$(C_1-C_6)$ alkylthio group;
(c4) a halo$(C_1-C_6)$alkylsulfinyl group;
(c5) a halo$(C_1-C_6)$alkylsulfonyl group; or
(c6) a halo$(C_1-C_6)$alkoxy group,
$R^5$ represents
(d1) a hydrogen atom;
(d3) a halo$(C_1-C_6)$alkoxy group;
(d5) a halo$(C_1-C_6)$alkylsulfinyl group; or
(d6) a halo$(C_1-C_6)$alkylsulfonyl group, and
m represents 0, 1, or 2, or
a salt thereof.

2. The benzimidazole compound or the salt thereof according to claim 1, wherein
$R^1$ and $R^2$ may be the same or different, and each represent
(a1) a hydrogen atom; or
(a2) a cyano group,
$R^3$ represents (b1) a hydrogen atom,
$R^4$ represents
(c1) a hydrogen atom;
(c2) a halogen atom;
(c3) a halo$(C_1-C_6)$alkylthio group; or
(c6) a halo$(C_1-C_6)$alkoxy group, and
$R^5$ represents
(d1) a hydrogen atom;
(d3) a halo$(C_1-C_6)$alkoxy group;
(d5) a halo$(C_1-C_6)$alkylsulfinyl group; or
(d6) a halo$(C_1-C_6)$alkylsulfonyl group.

3. The benzimidazole compound or the salt thereof according to claim 1, wherein
$R^1$ and $R^2$ each represent (a1) a hydrogen atom,
$R^3$ represents (b1) a hydrogen atom,
$R^4$ represents
(c1) a hydrogen atom;
(c3) a halo$(C_1-C_6)$alkylthio group; or
(c6) a halo$(C_1-C_6)$alkoxy group, and
$R^5$ represents
(d3) a halo$(C_1-C_6)$alkoxy group;
(d5) a halo$(C_1-C_6)$alkylsulfinyl group; or
(d6) a halo$(C_1-C_6)$alkylsulfonyl group.

4. The benzimidazole compound or the salt thereof according to claim 1, wherein
$R^1$ represents (a2) a cyano group,
$R^2$ represents (a1) a hydrogen atom,
$R^3$ represents (b1) a hydrogen atom,
$R^4$ represents
(c1) a hydrogen atom; or
(c3) a halo$(C_1-C_6)$alkylthio group, and
$R^5$ represents
(d3) a halo$(C_1-C_6)$alkoxy group;
(d5) a halo$(C_1-C_6)$alkylsulfinyl group; or
(d6) a halo$(C_1-C_6)$alkylsulfonyl group.

5. A composition comprising the benzimidazole compound or the salt thereof according to claim 1 as an active ingredient and at least one additive.

6. A method for using an agricultural or horticultural insecticide, the method comprising treating a plant or soil with an effective amount of the benzimidazole compound or the salt thereof according to claim 1.

7. A composition comprising the benzimidazole compound or the salt thereof according to claim 2 as an active ingredient and at least one additive.

8. A composition comprising the benzimidazole compound or the salt thereof according to claim 3 as an active ingredient and at least one additive.

9. A composition comprising the benzimidazole compound or the salt thereof according to claim 4 as an active ingredient and at least one additive.

10. A method for using an agricultural or horticultural insecticide, the method comprising treating a plant or soil with an effective amount of the benzimidazole compound or the salt thereof according to claim 2.

11. A method for using an agricultural or horticultural insecticide, the method comprising treating a plant or soil with an effective amount of the benzimidazole compound or the salt thereof according to claim 3.

12. A method for using an agricultural or horticultural insecticide, the method comprising treating a plant or soil with an effective amount of the benzimidazole compound or the salt thereof according to claim 4.

* * * * *